US011986356B2

(12) United States Patent
Sheeran et al.

(10) Patent No.: US 11,986,356 B2
(45) Date of Patent: May 21, 2024

(54) REDUCTION OF REVERBERATION ARTIFACTS IN ULTRASOUND IMAGES AND ASSOCIATED DEVICES, SYSTEMS, AND METHODS

(71) Applicant: KONINKLIJKE PHILIPS N.V., Eindhoven (NL)

(72) Inventors: Paul Sheeran, Woodinville, WA (US); Charles Tremblay-Darveau, Seattle, WA (US); Thanasis Loupas, Kirkland, WA (US); Allison Arden Daniels, Bothell, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 39 days.

(21) Appl. No.: 17/775,664

(22) PCT Filed: Nov. 17, 2020

(86) PCT No.: PCT/EP2020/082413
§ 371 (c)(1),
(2) Date: May 10, 2022

(87) PCT Pub. No.: WO2021/099320
PCT Pub. Date: May 27, 2021

(65) Prior Publication Data

US 2022/0401081 A1 Dec. 22, 2022

Related U.S. Application Data

(60) Provisional application No. 62/938,637, filed on Nov. 21, 2019.

(51) Int. Cl.
*A61B 8/08* (2006.01)
*G01S 7/52* (2006.01)

(52) U.S. Cl.
CPC .......... *A61B 8/5269* (2013.01); *G01S 7/5202* (2013.01); *G01S 7/52038* (2013.01)

(58) Field of Classification Search
CPC .. A61B 8/5269; G01S 7/5202; G01S 7/52038
See application file for complete search history.

(56) References Cited

U.S. PATENT DOCUMENTS 4,173,007 A 10/1979 McKeighen et al.
4,435,984 A * 3/1984 Gruber .................. G01N 29/07 73/628

(Continued)

FOREIGN PATENT DOCUMENTS

JP 2005152421 A 6/2005

OTHER PUBLICATIONS

International Search Report and Written Opinion for PCT/EP2020/082413; dated Jan. 21, 2021, 10 pages.

(Continued)

*Primary Examiner* — Dixomara Vargas

(57) ABSTRACT

Aspects of the present disclosure provide ultrasound systems and devices that provide for reduction of reverberation artifacts in ultrasound images by automatically changing imaging settings such as PRI or transmit/receive configuration based on detected amounts of reverberation in ultrasound images. In an exemplary embodiment, an apparatus includes a processor circuit in communication with an ultrasound probe. The processor circuit obtains a plurality of ultrasound images obtained using a plurality of different PRIs and/or pulse sequences, calculates an amount of reverberation artifacts in each of the plurality of ultrasound images, selects a pulse repetition interval and/or pulse sequence based on the amounts of reverberation artifacts in each of the plurality of ultrasound images, and controls the ultrasound transducer to obtain a reduced-reverberation ultrasound image using the selected pulse repetition interval (Continued)

300

Control an ultrasound transducer to obtain a plurality of ultrasound images using a respective plurality of pulse repetition intervals (PRIs)
310

Analyze the plurality of ultrasound images to calculate an amount of reverberation artifacts in each of the plurality of ultrasound images
320

Analyze the amounts of reverberation artifacts in each of the plurality of ultrasound images to select a PRI
330

In response to selecting the PRI, control the ultrasound transducer to obtain a reduced-reverberation ultrasound image at the selected PRI
340

Output the reduced-reverberation ultrasound image to a display
350 or pulse sequence. The reduced-reverberation ultrasound image is then output to a display.

20 Claims, 12 Drawing Sheets

(56) References Cited

U.S. PATENT DOCUMENTS

| | | | | |
|---|---|---|---|---|
| 6,210,328 | B1 * | 4/2001 | Robinson | G01S 7/5205 600/443 |
| 6,436,041 | B1 * | 8/2002 | Phillips | G01S 15/8963 600/458 |
| 6,544,177 | B1 * | 4/2003 | Robinson | G01S 15/8995 600/443 |
| 6,663,566 | B2 | 12/2003 | Pan et al. | |
| 2002/0116141 | A1 | 8/2002 | Mo et al. | |
| 2003/0045797 | A1 | 3/2003 | Christopher et al. | |
| 2003/0199763 | A1 * | 10/2003 | Angelsen | G01S 15/8927 600/437 |
| 2006/0036175 | A1 * | 2/2006 | Guracar | A61B 8/481 600/458 |
| 2010/0036244 | A1 * | 2/2010 | Angelsen | G01S 7/52077 600/438 |
| 2010/0114533 | A1 | 5/2010 | Fink et al. | |
| 2013/0204135 | A1 * | 8/2013 | Kucewicz | G06T 5/00 600/443 |
| 2013/0279294 | A1 * | 10/2013 | Angelsen | G01S 7/52042 367/87 |
| 2013/0343627 | A1 * | 12/2013 | Zwirn | A61B 8/5269 382/131 |
| 2014/0150556 | A1 * | 6/2014 | Angelsen | G01S 7/52038 73/596 |
| 2016/0235301 | A1 * | 8/2016 | Melodia | A61B 5/0024 |
| 2019/0353764 | A1 * | 11/2019 | Vignon | A61B 8/54 |
| 2021/0267577 | A1 * | 9/2021 | Trzasko | A61B 8/488 |
| 2023/0190230 | A1 * | 6/2023 | Yang | A61B 8/5269 600/437 |

OTHER PUBLICATIONS

Avdal, J. et al., "Effects of Reverberations and Clutter Filtering in Pulsed Doppler Using Sparse Sequences", IEEE transactions on ultrasonics, ferroelectrics, and frequency control, 2015, vol. 62, pp. 828-838.

Lin, F. et al., "Ultrasound contrast imaging: influence of scatterer motion in multi-pulse techniques", IEEE Trans Ultrason Ferroelectr Freq Control, 2013, vol. 60, No. 10, pp. 2065-2078.

* cited by examiner

402

452

REDUCTION OF REVERBERATION ARTIFACTS IN ULTRASOUND IMAGES AND ASSOCIATED DEVICES, SYSTEMS, AND METHODS

CROSS-REFERENCE TO PRIOR APPLICATIONS

This application is the U.S. National Phase application under 35 U.S.C. § 371 of International Application No. PCT/EP2020/082413, filed on Nov. 17, 2020, which claims the benefit of U.S. Provisional Patent Application No. 62/938,637, filed on Nov. 21, 2019. These applications are hereby incorporated by reference herein.

TECHNICAL FIELD

The present disclosure relates generally to the acquisition and processing of ultrasound images and, in particular, to systems and methods for reducing reverberation artifacts in ultrasound images obtained by ultrasound imaging devices.

BACKGROUND

Ultrasound imaging is frequently used to obtain images of internal anatomical structures of a patient. Ultrasound systems typically comprise an ultrasound transducer probe that includes a transducer array coupled to a probe housing. The transducer array is activated to vibrate at ultrasonic frequencies to transmit ultrasonic energy into the patient's anatomy, and then receive ultrasonic echoes reflected or backscattered by the patient's anatomy to create an image. Such transducer arrays may include various layers, including some with piezoelectric materials, which vibrate in response to an applied voltage to produce the desired pressure waves. These transducers may be used to successively transmit and receive several ultrasonic pressure waves through the various tissues of the body. The various ultrasonic responses may be further processed by an ultrasonic imaging system to display the various structures and tissues of the body.

An ultrasound transducer probe may be used to obtain ultrasound images in a variety of imaging modes, including standard B-mode imaging, harmonic imaging, and contrast imaging. One challenge for clinicians in viewing and analyzing ultrasound images is distinguishing portions of the images that are representative of artifacts or image clutter from actual tissue structures. One type of artifact that can occur in ultrasound imaging is reverberation. Some reverberation artifacts arise when vibrations from structures in the imaging field induced by previous transmit events interfere with a later receive line because the period between the transmit events, referred to as the pulse repetition interval (PRI), is too short to allow for the internal vibrations induced by previous pulses to subside or dissipate. Some ultrasound imaging systems allow for PRI to be manually adjusted. However, increasing the PRI (or, conversely, decreasing the pulse repetition frequency (PRF)) to reduce reverberation comes at the cost of lowered frame rate and increased blurring or clutter from tissue motion in between pulses. Another technique to reduce reverberations is to introduce additional transmit and/or receive events to sample and subtract reverberation, which does not require altering PRI but similarly reduces frame rate by increasing the total number of transmit/receive events per line. Thus, there is a trade-off between reducing reverberation artifacts and maintaining high temporal resolution. Further, although some systems allow for PRI adjustment, even well-trained clinicians are often generally unaware of PRI controls or prefer not to manipulate PRI.

SUMMARY

Aspects of the present disclosure provide ultrasound systems and devices that provide for reduction of reverberation artifacts in ultrasound images by automatically changing imaging settings such as PRI or transmit/receive configuration based on detected amounts of reverberation in ultrasound images. In an exemplary embodiment, an apparatus includes a processor circuit in communication with an ultrasound probe and configured to obtain a plurality of ultrasound images obtained using a plurality of different PRIs. The processor circuit computes and compares the amounts of reverberation artifacts in each image to select a PRI that reduces reverberation artifacts while also attempting to maintain the frame rate at acceptable levels. Automatically determining and/or adjusting imaging parameters such as PRI for the user advantageously improves workflow and increases confidence in the physician's analysis of the obtained ultrasound images.

In another exemplary embodiment, an apparatus includes a processor circuit in communication with an ultrasound probe and configured to compare ultrasound images obtained using at least two different ultrasound pulse sequences, at least one of which is configured to reduce reverberations. The processor circuit computes and compares the degree of reverberation between the current pulse sequence and the pulse sequence that is configured to reduce reverberation in order to select which sequence should be used to balance reverberation artifacts with loss in frame rate. Automatically determining and/or adjusting pulse sequence for the user advantageously improves workflow and increases confidence in the physician's analysis of the obtained ultrasound images.

In one embodiment, an apparatus for reducing reverberation artifacts in an ultrasound image includes: a processor circuit in communication with an ultrasound transducer, wherein the processor circuit is configured to: control the ultrasound transducer in communication with the processor circuit to obtain a plurality of ultrasound images using a respective plurality of pulse repetition intervals; calculate an amount of reverberation artifacts in each of the plurality of ultrasound images; select a pulse repetition interval based on the amounts of reverberation artifacts in each of the plurality of ultrasound images; in response to selecting the pulse repetition interval, control the ultrasound transducer to obtain a reduced-reverberation ultrasound image at the selected pulse repetition interval; and output the reduced-reverberation ultrasound image to a display in communication with the processor circuit.

In some embodiments, the processor circuit is configured to: identify a tissue portion and a non-tissue portion of each of the plurality of ultrasound images; calculate an intensity value for the non-tissue portion of each of the plurality of ultrasound images; and determine the amount of reverberation artifacts in each of the plurality of ultrasound images based on the calculated intensity values of the non-tissue portions of the plurality of ultrasound images. In some embodiments, the processor circuit is configured to calculate the intensity value for the non-tissue portion of each of the plurality of ultrasound images using a weighting algorithm, such that a first region of a respective ultrasound image near a focal point of the respective ultrasound image is assigned a greater weight than a second region of the respective ultrasound image away from the focal point of the respective ultrasound image. In some embodiments, the processor circuit is configured to: compare the amounts of reverberation artifacts in each of the plurality of ultrasound images to a threshold; and select the pulse repetition interval based on the comparison of the amounts of reverberation artifacts to the threshold. In some embodiments, the processor circuit is configured to determine the threshold based on the amount of reverberation artifacts in an ultrasound image of the plurality of ultrasound images associated with a maximum pulse repetition interval of the plurality of pulse repetition intervals. In some embodiments, the processor circuit is configured to select the pulse repetition interval based on: the comparison of the amounts of reverberations artifacts to the threshold; and a predetermined maximum pulse repetition interval In some embodiments, the apparatus further includes the ultrasound transducer. In some embodiments, the processor circuit is configured to: control the ultrasound transducer to obtain the plurality of images by performing a multi-pulse sequence to obtain a plurality of receive lines at a given location; sum the plurality of receive lines incoherently; and determine the amount of reverberation artifacts based on the incoherent summation of the plurality of receive lines. In some embodiments, the plurality of receive lines comprises a first receive line and a second receive line, and the processor circuit is configured to sum the plurality of receive lines incoherently by: computing: a first envelope for the first receive line; and a second envelope for the second receive line; weighting: the first envelope with a first summation weight; and the second envelope with a second summation weight; and incoherently summing the first weighted envelope and the second weighted envelope. In some embodiments, the first receive line corresponds to a first transmit pulse having a first amplitude, the second receive line corresponds to a second transmit pulse having a second amplitude, and the first and second summation weights are selected based on a ratio of a first amplitude of a first transmit pulse and a second amplitude of a second transmit pulse.

In some embodiments, a method for reducing reverberation artifacts in an ultrasound image includes: controlling an ultrasound transducer to obtain a plurality of ultrasound images using a respective plurality of pulse repetition intervals; calculating an amount of reverberation artifacts in each of the plurality of ultrasound images; selecting a pulse repetition interval based on the calculated amounts of reverberation artifacts in each of the plurality of ultrasound images; in response to selecting the pulse repetition interval, controlling the ultrasound transducer to obtain a reduced-reverberation ultrasound image at the selected pulse repetition interval; and outputting the reduced-reverberation ultrasound image to a display.

In some embodiments, the method further includes: identifying a tissue portion and a non-tissue portion of each of the plurality of ultrasound images; calculating an intensity value for the non-tissue portion of each of the plurality of ultrasound images; and calculating the amount of reverberation artifacts in each of the plurality of ultrasound images based on the calculated intensity values of the non-tissue portions of the plurality of ultrasound images. In some embodiments, calculating the intensity value for the non-tissue portion of each of the plurality of ultrasound images comprises calculating the intensity value for the non-tissue portion of each of the plurality of ultrasound images using a weighting algorithm, such that a first region of a respective ultrasound image near a focal point of the respective ultrasound image is assigned a greater weight than a second region of the respective ultrasound image away from the focal point of the respective ultrasound image.

In some embodiments, the method further includes: comparing the amounts of reverberation artifacts in each of the plurality of ultrasound images to a threshold; and selecting the pulse repetition interval comprises selecting the pulse repetition interval based on the comparison of the amounts of reverberation artifacts to the threshold. In some embodiments, the method further includes determining the threshold based on the amount of reverberation artifacts in an ultrasound image of the plurality of ultrasound images associated with a maximum pulse repetition interval of the plurality of pulse repetition intervals. In some embodiments, selecting the pulse repetition interval comprises selecting the pulse repetition interval based on: the comparison of the amounts of reverberations artifacts to the threshold; and a predetermined maximum pulse repetition interval. In some embodiments, controlling the ultrasound transducer to obtain the plurality of ultrasound images comprises: performing a multi-pulse sequence to obtain a plurality of receive lines at a given location; summing the plurality of receive lines incoherently; and determining the amount of reverberation artifacts based on the incoherent summation of the plurality of receive lines. In some embodiments, the plurality of receive lines comprises a first receive line and a second receive line, and summing the plurality of receive lines incoherently comprises: computing: a first envelope for the first receive line; and a second envelope for the second receive line; weighting: the first envelope with a first summation weight; and the second envelope with a second summation weight; and incoherently summing the first weighted envelope and the second weighted envelope. In some embodiments, the first receive line corresponds to a first transmit pulse having a first amplitude, the second receive line corresponds to a second transmit pulse having a second amplitude, and the first and second summation weights are selected based on a ratio of a first amplitude of a first transmit pulse and a second amplitude of a second transmit pulse.

In another embodiment, an apparatus for selecting a pulse sequence associated with reduced reverberation artifacts includes: a processor circuit in communication with an ultrasound transducer, wherein the processor circuit is configured to: control the ultrasound transducer in communication with the processor circuit to obtain a first ultrasound image using a first pulse sequence; control the ultrasound transducer to obtain a second ultrasound image using a second pulse sequence; calculate an amount of reverberation artifacts in each of the first ultrasound image and the second ultrasound image; compare the amounts of reverberation artifacts of the first ultrasound image and the second ultrasound image; select a pulse sequence based on the comparison of the amounts of reverberation artifacts; control the ultrasound transducer to obtain a reduced-reverberation ultrasound image using the selected pulse sequence; and output the reduced-reverberation ultrasound image to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
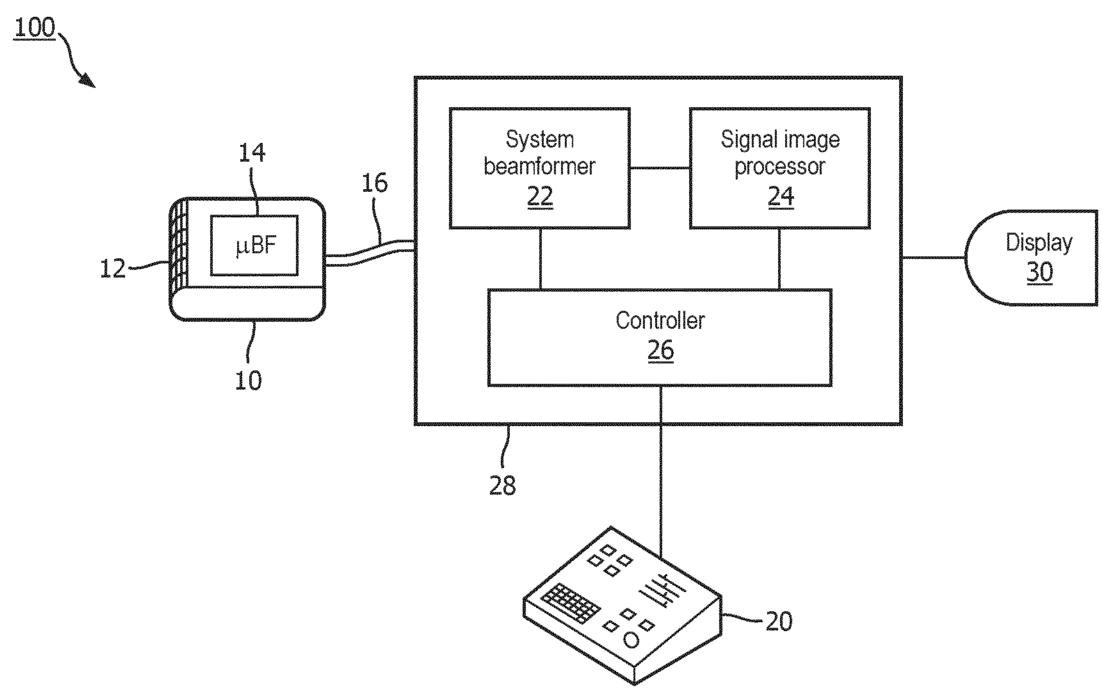
FIG. 1 is a schematic diagram of an ultrasound imaging system, according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In FIG. 1, an ultrasound system 100 according to embodiments of the present disclosure is shown in block diagram form. An ultrasound probe 10 has a transducer array 12 comprising a plurality of ultrasound transducer elements or acoustic elements. In some instances, the array 12 may include any number of acoustic elements. For example, the array 12 can include between 1 acoustic element and 100000 acoustic elements, including values such as 2 acoustic elements, 4 acoustic elements, 36 acoustic elements, 64 acoustic elements, 128 acoustic elements, 300 acoustic elements, 812 acoustic elements, 3000 acoustic elements, 9000 acoustic elements, 30,000 acoustic elements, 65,000 acoustic elements, and/or other values both larger and smaller. In some instances, the acoustic elements of the array 12 may be arranged in any suitable configuration, such as a linear array, a planar array, a curved array, a curvilinear array, a circumferential array, an annular array, a phased array, a matrix array, a one-dimensional (1D) array, a 1.X dimensional array (e.g., a 1.5D array), or a two-dimensional (2D) array. The array of acoustic elements (e.g., one or more rows, one or more columns, and/or one or more orientations) can be uniformly or independently controlled and activated. The array 12 can be configured to obtain one-dimensional, two-dimensional, and/or three-dimensional images of patient anatomy.

Although the present disclosure refers to synthetic aperture external ultrasound imaging using an external ultrasound probe, it will be understood that one or more aspects of the present disclosure can be implemented in any suitable ultrasound imaging probe or system, including external ultrasound probes and intraluminal ultrasound probes. For example, aspects of the present disclosure can be implemented in ultrasound imaging systems using a mechanically-scanned external ultrasound imaging probe, an intracardiac (ICE) echocardiography catheter and/or a transesophageal echocardiography (IEE) probe, a rotational intravascular ultrasound (IVUS) imaging catheter, a phased-array IVUS imaging catheter, a transthoracic echocardiography (TTE) imaging device, or any other suitable type of ultrasound imaging device.

Figure 2:
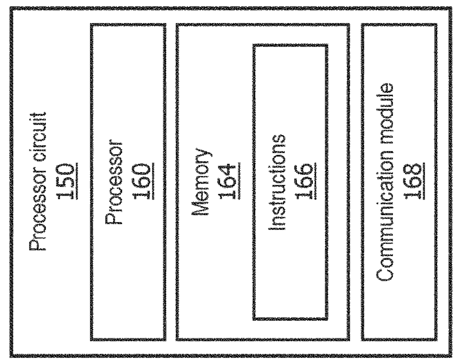
FIG. 2 is a schematic diagram of a processor circuit, according to embodiments of the present disclosure.

Referring again to FIG. 1, the acoustic elements of the array 12 may comprise one or more piezoelectric/piezoresistive elements, lead zirconate titanate (PZT), piezoelectric micromachined ultrasound transducer (PMUT) elements, capacitive micromachined ultrasound transducer (CMUT) elements, and/or any other suitable type of acoustic elements. The one or more acoustic elements of the array 12 are in communication with (e.g., electrically coupled to) electronic circuitry 14. In some embodiments, such as the embodiment of FIG. 1, the electronic circuitry 14 can comprise a microbeamformer (pBF). In other embodiments, the electronic circuitry comprises a multiplexer circuit (MUX). The electronic circuitry 14 is located in the probe 10 and communicatively coupled to the transducer array 12. In some embodiments, one or more components of the electronic circuitry 14 can be positioned in the probe 10. In some embodiments, one or more components of the electronic circuitry 14, can be positioned in a computing device or processing system 28. The computing device 28 may be or include a processor, such as one or more processors in communication with a memory. As described further below, the computing device 28 may include a processor circuit as illustrated in FIG. 2. In some aspects, some components of the electronic circuitry 14 are positioned in the probe 10 and other components of the electronic circuitry 14 are positioned in the computing device 28. The electronic circuitry 14 may comprise one or more electrical switches, transistors, programmable logic devices, or other electronic components configured to combine and/or continuously switch between a plurality of inputs to transmit signals from each of the plurality of inputs across one or more common communication channels. The electronic circuitry 14 may be coupled to elements of the array 12 by a plurality of communication channels. The electronic circuitry 14 is coupled to a cable 16, which transmits signals including ultrasound imaging data to the computing device 28.

In the computing device 28, the signals are digitized and coupled to channels of a system beamformer 22, which appropriately delays each signal. The delayed signals are then combined to form a coherent steered and focused receive beam. System beamformers may comprise electronic hardware components, hardware controlled by software, or a microprocessor executing beamforming algorithms. In that regard, the beamformer 22 may be referenced as electronic circuitry. In some embodiments, the beamformer 22 can be a system beamformer, such as the system beamformer 22 of FIG. 1, or it may be a beamformer implemented by circuitry within the ultrasound probe 10. In some embodiments, the system beamformer 22 works in conjunction with a microbeamformer (e.g., electronic circuitry 14) disposed within the probe 10. The beamformer 22 can be an analog beamformer in some embodiments, or a digital beamformer in some embodiments. In the case of a digital beamformer, the system includes A/D converters which convert analog signals from the array 12 into sampled digital echo data. The beamformer 22 generally will include one or more microprocessors, shift registers, and or digital or analog memories to process the echo data into coherent echo signal data. Delays are effected by various means such as by the time of sampling of received signals, the write/read interval of data temporarily stored in memory, or by the length or clock rate of a shift register as described in U.S. Pat. No. 4,173,007 to McKeighen et al., the entirety of which is hereby incorporated by reference herein. Additionally, in some embodiments, the beamformer can apply appropriate weight to each of the signals generated by the array 12. The beamformed signals from the image field are processed by a signal and image processor 24 to produce 2D or 3D images for display on an image display 30. The signal and image processor 24 may comprise electronic hardware components, hardware controlled by software, or a microprocessor executing image processing algorithms. It generally will also include specialized hardware or software which processes received echo data into image data for images of a desired display format such as a scan converter. In some embodiments, beamforming functions can be divided between different beamforming components. For example, in some embodiments, the system 100 can include a microbeamformer located within the probe 10 and in communication with the system beamformer 22. The microbeamformer may perform preliminary beamforming and/or signal processing that can reduce the number of communication channels required to transmit the receive signals to the computing device 28.

Control of ultrasound system parameters such as scanning mode (e.g., B-mode, M-mode), probe selection, beam steering and focusing, and signal and image processing is done under control of a system controller 26 which is coupled to various modules of the system 100. The system controller 26 may be formed by application specific integrated circuits (ASICs) or microprocessor circuitry and software data storage devices such as RAMs, ROMs, or disk drives. In the case of the probe 10, some of this control information may be provided to the electronic circuitry 14 from the computing device 28 over the cable 16, conditioning the electronic circuitry 14 for operation of the array as required for the particular scanning procedure. The user inputs these operating parameters by means of a user interface device 20.

In some embodiments, the image processor 24 is configured to generate images of different modes to be further analyzed or output to the display 30. For example, in some embodiments, the image processor can be configured to compile a B-mode image, such as a live B-mode image, of an anatomy of the patient. In other embodiments, the image processor 24 is configured to generate or compile an M-mode image. An M-mode image can be described as an image showing temporal changes in the imaged anatomy along a single scan line.

It will be understood that the computing device 28 may comprise hardware circuitry, such as a computer processor, application-specific integrated circuit (ASIC), field-programmable gate array (FPGA), capacitors, resistors, and/or other electronic devices, software, or a combination of hardware and software. In some embodiments, the computing device 28 is a single computing device. In other embodiments, the computing device 28 comprises separate computer devices in communication with one another.

FIG. 2 is a schematic diagram of a processor circuit 150, according to embodiments of the present disclosure. The processor circuit 150 may be implemented in the computing device 28, the signal and image processor 24, the controller 26, and/or the probe 10 of FIG. 1. As shown, the processor circuit 150 may include a processor 160, a memory 164, and a communication module 168. These elements may be in direct or indirect communication with each other, for example via one or more buses.

The processor 160 may include a central processing unit (CPU), a digital signal processor (DSP), an ASIC, a controller, an FPGA, another hardware device, a firmware device, or any combination thereof configured to perform the operations described herein. The processor 160 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 160), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 160, cause the processor 160 to perform the operations described herein with reference to the processor 28 and/or the probe 10 (FIG. 1). Instructions 166 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 168 can include any electronic circuitry and/or logic circuitry to facilitate direct or indirect communication of data between the processor 28, the probe 10, and/or the display 30. In that regard, the communication module 168 can be an input/output (I/O) device. In some instances, the communication module 168 facilitates direct or indirect communication between various elements of the processor circuit 150 and/or the processing system 106 (FIG. 1A).

As mentioned above, ultrasound images can include a number of undesirable artifacts, including reverberation artifacts. Reverberation artifacts may be particularly undesirable in certain ultrasound imaging modalities, such as contrast imaging, in which a physician desires to visualize blood flow below the skin layer. In many cases, it may be desirable to operate at the fastest frame-rate possible by minimizing the pulse repetition interval (PRI) and using as few pulses as possible in a multi-pulse sequence. One factor that leads to the presence of some reverberation artifacts in an image is an insufficient PRI between the pulses used in obtaining ultrasound images, which allows echoes from deep structures beyond the imaging region to be received with a later receive line. Because acoustic reverberation takes time to dissipate in tissue and anatomical structures, the short PRI that maximizes frame rate may cause an artifact in the ultrasound image appearing as evenly-spaced lines or diffuse noise that appears within the imaging region. One method to reduce these artifacts is to simply increase PRI at the expense of frame-rate. Although some systems allow for the PRI to be changed, adjusting the PRI may be too complex for some physicians, who may not understand the physical principles behind reverberation and PRI. Thus, some physicians may avoid adjusting PRI. With the PRI unchanged, the physician may attempt to distinguish between true structures in the ultrasound image and reverberation artifacts, which may be difficult and imprecise. Another method to reduce these artifacts may be to alter the multi-pulse sequence to better sample and eliminate reverberation, often by introducing additional transmit and/or receive events at the expense of frame-rate. Systems do not typically allow the user to change the pulse configuration in response to reverberation, and so the system designer may choose a preferred sequence to either allow reverb and maximize frame-rate or reduce reverb and accept a lower frame-rate as a result.

Accordingly, the present disclosure provides devices, systems and methods for automatically adjusting imaging settings such as PRI and pulse sequence configuration to reduce reverberation artifacts in an ultrasound image. In that regard, the amount of reverberation artifacts in an image may be associated with the PRI or the pulse configuration of the imaging sequence. Thus, the present application describes embodiments of systems and methods for automatically adjusting PRI and/or pulse configuration in a manner that specifically achieves a reduction in reverberation artifacts. The automatic adjustment may be performed to maintain the frame rate of the imaging sequence at or above a particular level acceptable to a user. In that regard, embodiments of the present disclosure involve identifying reverberation in one or more ultrasound images, and automatically selecting a PRI and/or switching to an alternative pulse sequence based on the identification of reverberation artifacts. For example, devices, systems, and methods are provided that quantify reverberation artifacts in ultrasound images obtained using different PRIs, analyze the quantified reverberation artifacts for each image to select a PRI that reduces reverberation artifacts, and control the ultrasound probe to acquire images using the selected PRI to obtain reverberation-reduced ultrasound images.

Figure 3:
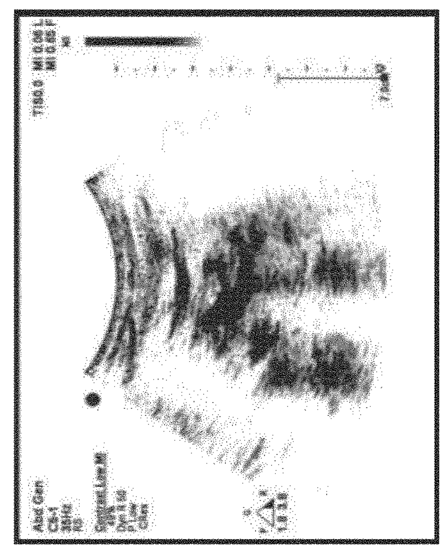
FIG. 3 is an ultrasound image of a region of a patient's body, the ultrasound image including reverberation artifacts, according to aspects of the present disclosure.

FIG. 3 is an ultrasound image obtained by an external ultrasound imaging system. The image 200 is obtained of an anatomical region of a patient's body and shows a skin region 210 and reverberation region 220 at a deeper depth relative to the skin region. The skin region 210 may be associated with non-reverb signals, or true signals reflected from the skin and/or other tissue structures. By contrast, some or all of the reverberation region 220 may be associated with acoustic reverberation, and therefore does not reflect the actual tissue structures in the anatomy. The artifacts and clutter in the reverberation region 220 may undesirably affect the ability of physicians to visualize anatomical structures and make diagnoses. Accordingly, confidence in diagnoses may be reduced.

Figure 4:
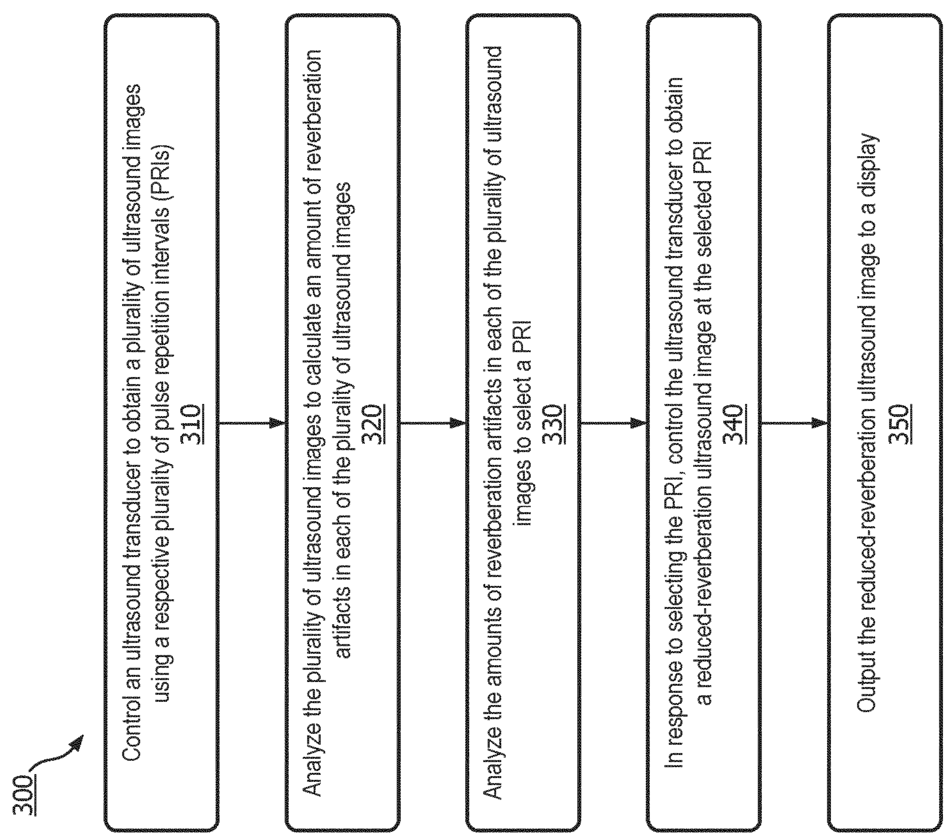
FIG. 4 is a flow diagram illustrating a method for reducing reverberation artifacts in an ultrasound image, according to aspects of the present disclosure.

FIG. 4 is a flow chart illustrating a method 300 for reducing reverberation artifacts in ultrasound images, according to an embodiment of the present disclosure. It will be understood that one or more steps of the method 300 may be performed by the ultrasound imaging system 100 shown in FIG. 1, and/or the processor circuit 150 shown in FIG. 2, for example. In step 310, an ultrasound transducer is controlled to obtain a plurality of ultrasound images using a respective plurality of pulse repetition intervals (PRIs). In some embodiments, the ultrasound transducer comprises an external ultrasound probe that includes an array of ultrasound transducer elements. However, the method 300 may be performed with other types of ultrasound transducers, including intravascular ultrasound (IVUS) devices, intracardiac echocardiography (ICE) catheters, transesophageal echocardiography (TEE) probes, transthoracic echocardiography (TTE) probes, or any other suitable ultrasound imaging device. In some embodiments, the system may comprise a user input device, such as a mouse, keyboard, touch screen, and/or any other suitable user input device. The method 300 may be initiated by a user via the user input device. For example, in some embodiments, the method 300 is initiated by the user pressing or selecting a button or icon, such as an icon on a touch screen display. In some embodiments, once initiated, the method 300 proceeds to perform each step of the method 300 automatically. In some embodiments, one or more steps of the method 300 are performed in the background such that the one or more steps of the method 300 are not shown on a display. In some embodiments, one or more steps of the method are shown on a display device such that a user or operator can monitor the progress of the method 300.

In an exemplary embodiment, each of the plurality of ultrasound images is obtained using a different PRI. For example, the PRIs may comprise a set of PRIs that vary incrementally. Any suitable number of ultrasound images and corresponding PRIs may be used in step 310, including the standard two-way travel time (time of flight) for the acoustic wave in the imaging window plus 2, 3, 4, 5, 6, 8, 10, 12, 15, 20, 30, 50, or any other suitable number of microseconds, both larger and smaller. PRIs may be represented or measured in time (e.g., μs, ms), in depth or distance (e.g., mm), in pixels, or any other suitable unit of measurement. In some embodiments, the PRIs vary between a minimum PRI and a maximum PRI. In some embodiments, the minimum PRI is 0, such that there is effectively no gap or rest time between pulses, beyond the standard two-way travel time for the acoustic wave. In some embodiments, the minimum PRI is based on the hardware capabilities of the ultrasound transducer to switch from receiving to transmitting. In some embodiments, the minimum PRI is predetermined by the manufacturer of the processor circuit and/or the ultrasound transducer to represent a minimum amount of time to allow vibrations in the tissue and/or the ultrasound transducer to dissipate before transmitting the next pulse. In some embodiments, the maximum PRI is predetermined, selected, or otherwise configured in the processor circuit based on various imaging factors, including the particular scan sequence used (e.g., multi-pulse, pulse inversion, single pulse, etc.), the desired imaging depth or focal zone, and/or a minimum frame rate. In some embodiments, the different PRIs used to obtain the plurality of ultrasound images vary in constant increments. In other embodiments, the different PRIs vary in a non-constant or non-linear fashion. In some embodiments, only one ultrasound image is obtained for each PRI in step 310. In other embodiments, multiple images are obtained for each PRI.

In step 320, the plurality of ultrasound images is analyzed to calculate an amount of reverberation artifacts in each of the plurality of ultrasound images. In the context of the present disclosure, analyzing ultrasound images may refer to performing signal processing on the electrical signals output by the transducer array and/or image processing on the image data generated from the electrical signals output by the transducer array. In some embodiments, the amount of reverberation artifacts in an image can be quantified or inferred by removing or suppressing tissue in the image, and summing the remaining signal or intensity in the image. The summed remaining signal may represent or correlate to the amount of reverberation artifacts present in the image, and may also represent other artifacts. In some embodiments, the amount of intensity, or intensity value, for the non-tissue portion of each ultrasound image is calculated using a weighting algorithm. The weighting algorithm may be applied such that particular regions of the ultrasound images are given more weight compared to other regions. For example, in some embodiments, the non-tissue signal intensity in a region of an ultrasound image near a focal point of the ultrasound transducer is given greater weight than regions that are positioned away from the focal point.

Accordingly, in some embodiments, the plurality of ultrasound images is analyzed to distinguish between a tissue portion and a non-tissue portion in each of the plurality of ultrasound images. Each ultrasound image may then be analyzed to calculate the remaining overall intensity value. The amount of reverberation artifacts may be determined for each ultrasound image based on based on the calculated intensity value. In other embodiments, reverberation detection algorithms can be used to distinguish between reverberation artifacts and other contributions to an image. Because the ultrasound images are obtained using different PRIs, it may be expected that the amount of reverberation artifacts changes based on the PRI associated with a particular image.

In step 330, the amounts of reverberation artifacts in each of the plurality of ultrasound images are analyzed to select a PRI. In some embodiments, analyzing the amounts of reverberation artifacts comprises comparing the amounts of reverberation artifacts. For example, the amounts of reverberation artifacts in each image may be compared to a threshold. As explained further below, the threshold may be determined based on a minimum intensity image and/or a maximum PRI image. In other embodiments, the amounts of reverberation artifacts in each image are compared to the amounts of reverberation artifacts in the other images. Based on the comparison and/or analysis, a PRI is selected that is associated with reduced reverberation artifacts. For example, the selected PRI may be the PRI that is closest to, without exceeding, the threshold. In other embodiments, the selected PRI is determined based on a mean, median, statistical distribution (e.g., gaussian), or any other suitable statistically significant value determined based on a comparison of the intensity values of the plurality of images. In some embodiments, the PRI may be selected such that it does not exceed a predetermined maximum PRI. The predetermined maximum PRI may be determined by the manufacturer such that the frame rate of the ultrasound images does not fall below a lower-limit. In some embodiments, the predetermined maximum PRI may change based on the imaging modality used, the imaging depth, and/or other imaging parameters.

In many instances, the selected PRI associated with the reduced reverberation artifacts may be higher than a PRI initially used, which may result in reduced frame rate. However, while reverberation artifacts may decrease with increased PRI, it may be undesirable to select a PRI that is too high, resulting in unsatisfactory frame rates. As mentioned above, in some instances, a physician may prefer to maintain the frame rate above some amount even if some reverberation artifacts remain. Accordingly, the PRI may be selected in a manner that balances the interest of reducing reverberation artifacts with the interest of maintaining high frame rates. For example, in some aspects, the system may be configured to select only PRIs that are at or below a predetermined maximum PRI. Further, the system may be configured to establish or determine a threshold based on a minimum amount of reverberation detected in the plurality of images, such that some satisfactory amount of reverberation is allowed in order to maintain sufficiently high frame rates for the imaging application.

In step 340, in response to selecting the PRI, the ultrasound transducer is controlled to obtain a reduced-reverberation ultrasound image at the selected PRI. In step 350, the reduced-reverberation ultrasound image is output to a display. It will be understood that the steps of the method 300 may be performed repetitiously to produce and display a live view or stream of reduced-reverberation ultrasound images. Further, in some embodiments, the method 300 may be halted by a user by selecting a user input on the user input device. For example, if the particular imaging application or modality is not likely to produce reverberation, the user may terminate the method 300 to return the PRI to a default or initial value.

Figure 5:
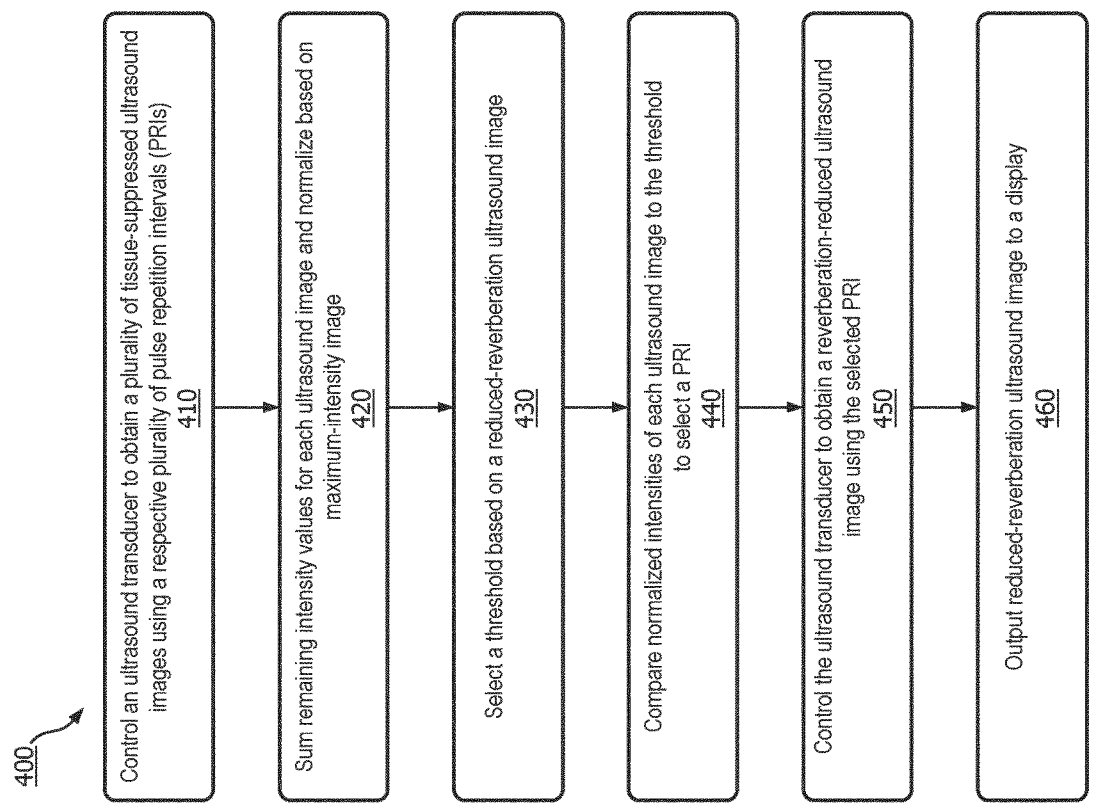
FIG. 5 is a flow diagram illustrating a method for reducing reverberation artifacts in an ultrasound image, according to aspects of the present disclosure.

FIG. 5 is a flow chart illustrating a method 400 for reducing reverberation artifacts in ultrasound images, according to an embodiment of the present disclosure. It will be understood that one or more steps of the method 400 may be performed by the ultrasound imaging system 100 shown in FIG. 1, and/or the processor circuit 150 shown in FIG. 2, for example. In some aspects, one or more steps of the method 400 may be used in performing the method 300 shown in FIG. 4. In step 410, a processor circuit or processing system controls an ultrasound transducer to obtain a plurality of tissue-suppressed ultrasound images using a respective plurality of PRIs. In some aspects, the processor circuit may be configured to suppress tissue in ultrasound images using image processing techniques. In some aspects, the processor circuit may receive a user input via a user input device that initiates a tissue suppression protocol. In some embodiments, the tissue suppression protocol is automatically activated as part of a reverberation reduction protocol. In that regard, in some embodiments, the method 400 is initiated by a user input, and proceeds to perform each step of the method 400 automatically. In some embodiments, one or more steps of the method 400 are performed in the background such that the one or more steps of the method 400 are not shown on a display.

Figure 6:
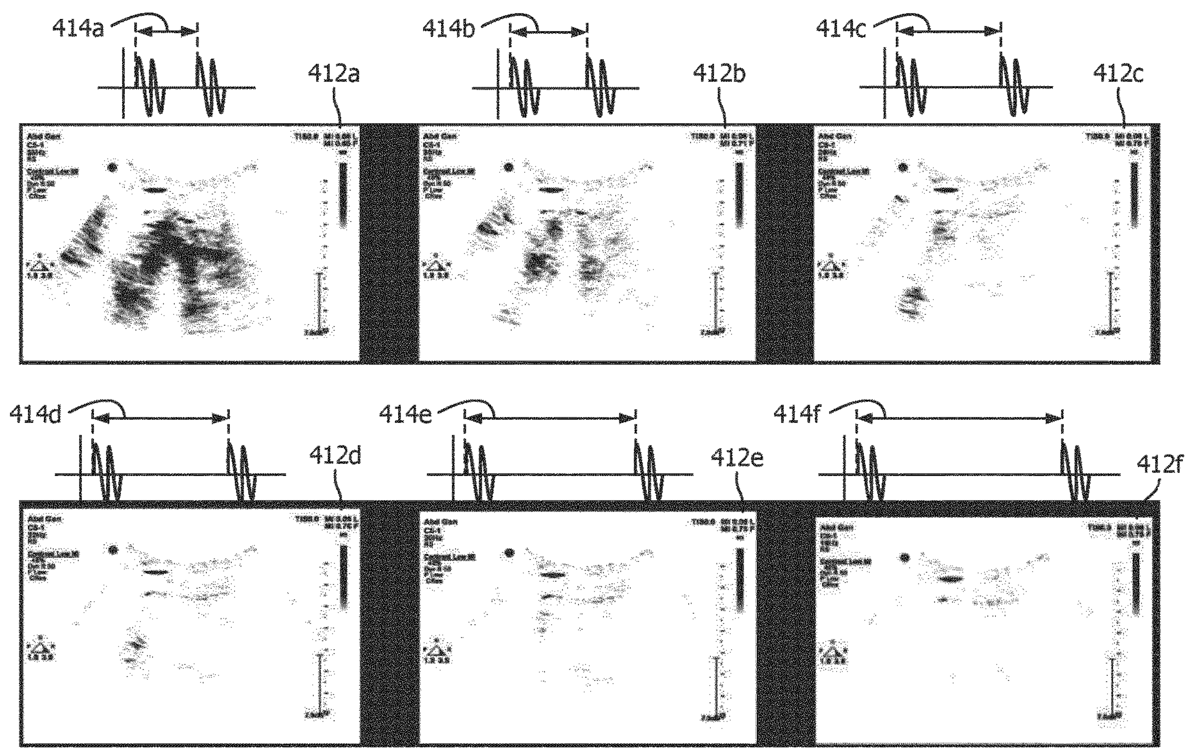
FIG. 6 is a set of ultrasound images obtained using a plurality of pulse repetition intervals, according to aspects of the present disclosure.

FIG. 6 includes a plurality of ultrasound images obtained during step 410 of the method 400. In that regard, each of a plurality of tissue-suppressed ultrasound images 412*a*-412*f* is obtained using a respective PRI 414*a*-414*f*. The respective PRIs 414*a*-414*f* are illustrated as the spacing, in time, between successive transmit pulses. In the embodiment of FIG. 6, each PRI 414 is illustrated as the spacing between the beginning of successive transmit pulses. However, in other embodiments, the PRI 414 may be defined by the distance between the center or end of successive transmit pulses, for example. In FIG. 6, it can be seen that as the PRI 414 increases, the overall intensity or bright portions in the ultrasound images 412 decreases. Because the tissue has been suppressed in the ultrasound images 412, it may be inferred that the remaining portions are likely due to image clutter, such as reverberation artifacts. Thus, by increasing the PRI, more time is allowed for reverberation in the anatomy to dissipate, and less reverberation artifacts are visible. Accordingly, the ultrasound image 412*f*, which was obtained using the greatest PRI 414*f*, has the least amount of remaining reverberation artifacts.

Referring again to FIG. 5, in step 420, the processor circuit sums the remaining intensity values of the tissue-suppressed ultrasound images and normalizes the summed intensity values of each ultrasound image. The processor circuit is configured to normalize the summed intensity values based on a minimum intensity value of a minimum intensity image of the plurality of ultrasound images. However, in other embodiments, the processor circuit is configured to normalize to other values, such as a maximum intensity value image, a mean summed intensity value, or a predetermined intensity value. In step 430, a threshold is selected or determined based on the summed intensity values of the ultrasound images. For example, the threshold may be selected based on an ultrasound image containing minimal reverberation. For example, referring to FIG. 6, the threshold may be selected based on the ultrasound image 412*f*, which includes the lowest amount of reverberation artifacts and/or lowest amount of overall remaining image intensity. In other embodiments, the threshold 432 is selected based on the ultrasound image associated with the greatest PRI.

Figure 7:
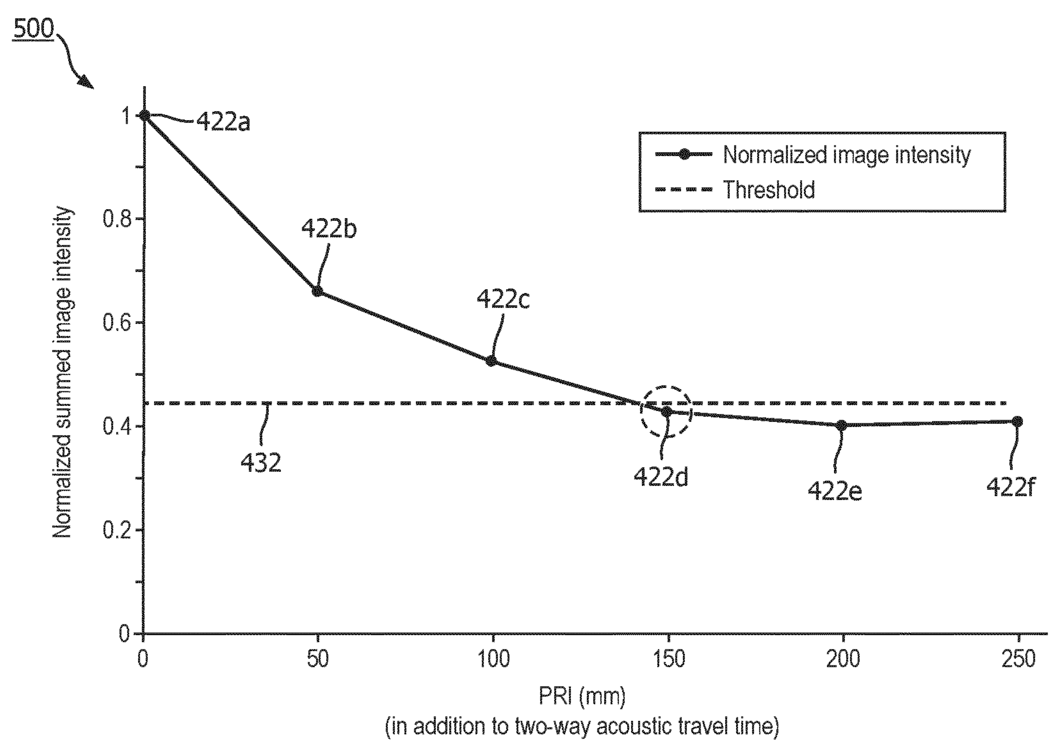
FIG. 7 is a graph of quantified reverberation artifacts in ultrasound images obtained at the plurality of pulse repetition intervals shown in FIG. 6, according to aspects of the present disclosure.

In step 440, the normalized intensity values for each ultrasound image calculated in step 420 are compared to the threshold to select a desired PRI. In that regard, FIG. 7 is a graph 500 illustrating aspects of steps 420-440. For example, the graph or plot 500 shows the summed and normalized intensity values 422*a*-422*f* of the tissue suppressed images 412*a*-412*f* relative to a threshold 432, with PRI as the x-axis. In FIG. 7, the additional PRI increment is represented by a representation in millimeters of depth. However, other units of measurement may be used for PRIs, including units of time, pixels, or any other suitable type of measurement. As can be seen, the PRIs, which in FIG. 7, represent the additional delay beyond the minimum two-way acoustic travel time of the PRI, are associated with the normalized intensity values 422*a*-422*f* of the ultrasound images range from 0 mm to 250 mm, increasing incrementally by 50 mm. In other words, with reference to FIG. 7, a PRI of 0 mm represents a minimum PRI having no additional delay or buffer beyond the two-way acoustic travel time associated with the acoustic pulses. In other embodiments, the plurality PRIs are not incrementally and evenly spaced, as they are shown in FIG. 7. For example, in some embodiments, the PRIs differ by varying amounts, such as 10 mm, 20 mm, 25 mm, 30 mm, 100 mm, and/or any other suitable increment, both larger and smaller.

Referring to FIGS. 5-7, the threshold 432 may be determined based on a minimum intensity tissue-suppressed ultrasound image, such as 412*f*. The threshold 432 may be determined based on a percentage of the normalized, summed intensity of the minimum intensity ultrasound image (e.g., 412*f*). For example, in the embodiment of FIG. 7, the threshold 432 may be determined by adding 3% of the normalized, summed intensity of the ultrasound image 412*f*. In other embodiments, the threshold 432 is determined by adding 1%, 2%, 5%, 10%, or any other suitable percentage of the normalized, summed intensity of an ultrasound image, both larger and smaller. The desired PRI is selected by identifying the PRI associated with the normalized intensity value that is closest to, without exceeding, the threshold 432. In FIG. 7, the desired or selected PRI is 150 mm, which is associated with the normalized intensity value 422*d*. In other embodiments, the desired PRI is selected by identifying the PRI associated with the normalized intensity value that is closest to the threshold 432, whether the respective PRI exceeds the threshold 432 or not. In some embodiments, the desired PRI is determined based on an interpolation between two or more PRIs. In some embodiments, the desired PRI is selected by computing a best fit line or curve for two or more of the normalized intensity values 422, and determining an intersection point between the threshold 432 and the best fit line or curve.

In step 450, the ultrasound transducer is controlled, set, or configured to obtain one or more reduced-reverberation ultrasound images at the selected PRI. In some embodiments, the method 400 further includes configuring the system to retain the tissue features that were previously reduced, suppressed, or discarded in step 410. In some embodiments, this involves deactivating a tissue suppression feature. In some embodiments, the tissue suppression feature may include a protocol or set of instructions stored on a memory that is part of an image processing sequence or computer program. In some embodiments, the tissue suppression feature is deactivated automatically, and the ultrasound transducer is configured with the selected PRI automatically, in response to selecting the PRI. In some embodiments, an operator deactivates the tissue suppression feature. In step 460, the one or more reduced-reverberation ultrasound images are output to a display.

Figure 8A:
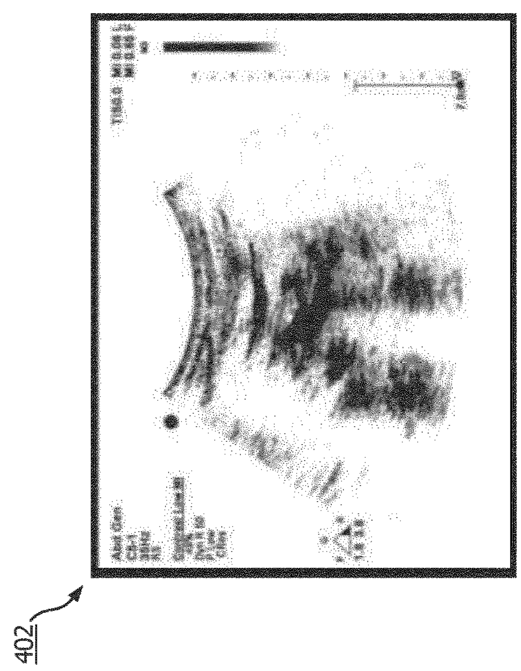
FIG. 8A is an original ultrasound image of a region of a patient's body, the ultrasound image including reverberation artifacts, according to aspects of the present disclosure.
Figure 8B:
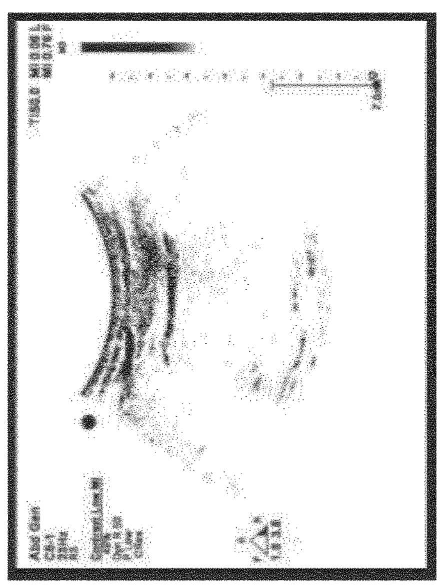
FIG. 8B is a reduced-reverberation ultrasound image of the region of the patient's body, the reduced-reverberation ultrasound image obtained using a PRI selected using a method for reducing reverberation artifacts, according to aspects of the present disclosure.

FIGS. 8A and 8B illustrate the reverberation-reduction effect of the method 300 and/or the method 400 in an ultrasound imaging procedure. In that regard, FIG. 8A shows an image 402 before applying the reverberation-reduction techniques. In that regard, the image 402 of FIG. 8A may be obtained using a default or initial PRI. For the image 402, the initial PRI may be significantly shorter than that used in FIG. 8B, such that a significant amount of reverberation artifacts is present in the region 442 of the image 402. As mentioned above, these reverberation artifacts may be particularly undesirable in contrast imaging procedures used to indicate and/or quantify blood flow in the region 442. FIG. 8B shows an ultrasound image 452 obtained using the reverberation techniques described above with respect to the methods 300 and/or 400. In that regard, the image 452 of FIG. 8B includes the same image features and imaging region of the image 402 shown in FIG. 8A, but taken with an adjusted PRI automatically selected and set according to the methods 300 and/or 400 described above. Accordingly, reverberation artifacts are significantly reduced or eliminated in the region 462 of the image 452 while the tissue features remain present.

Figure 9:
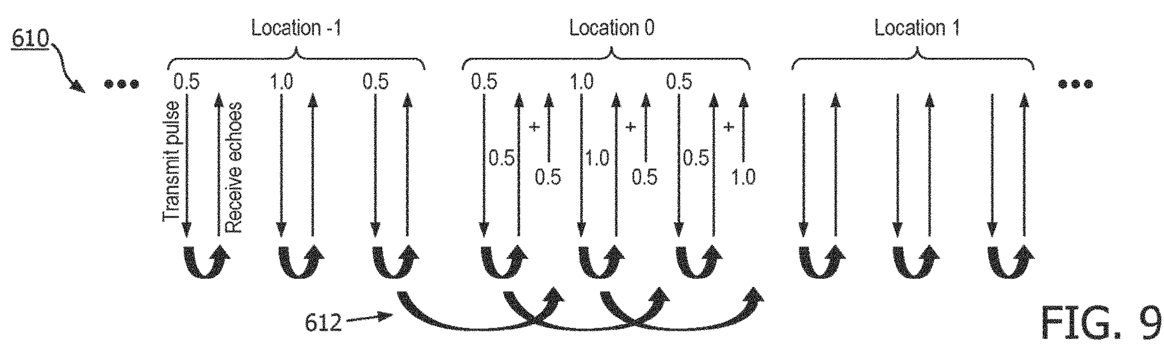
FIG. 9 is a diagrammatic view of reverberation in an amplitude modulation multi-pulse ultrasound imaging sequence, according to aspects of the present disclosure.
Figure 10:
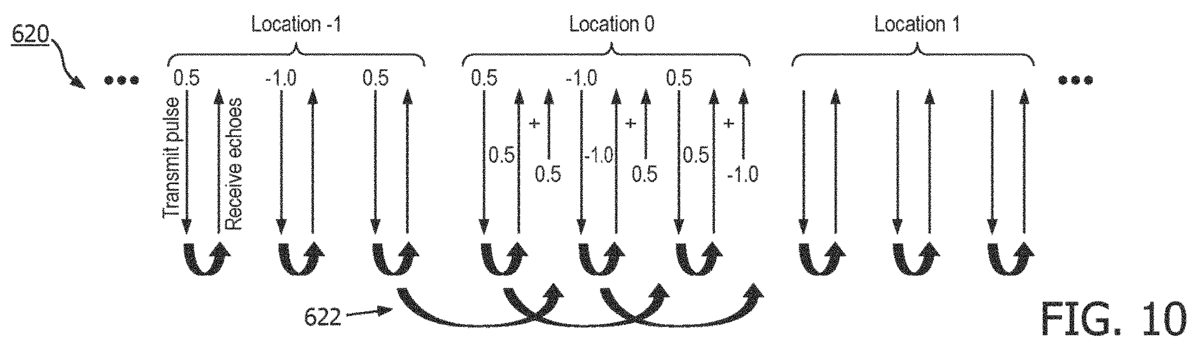
FIG. 10 is a diagrammatic view of reverberation in an amplitude modulation pulse inversion multi-pulse ultrasound imaging sequence, according to aspects of the present disclosure.
Figure 11:
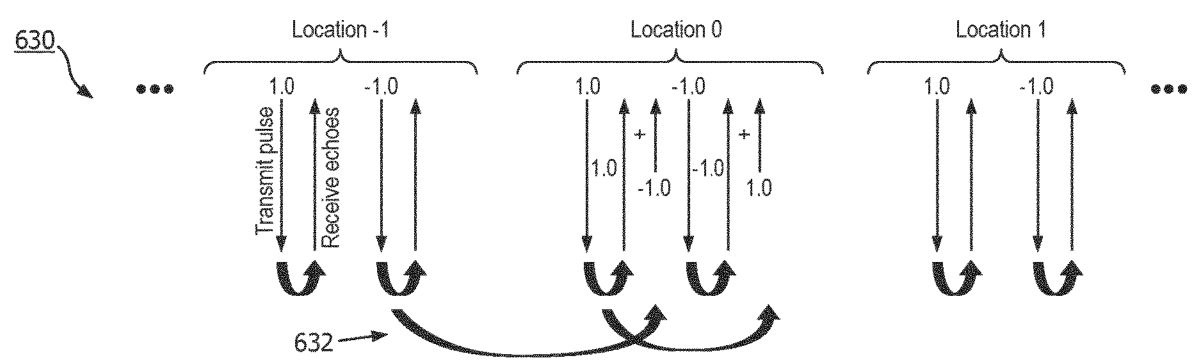
FIG. 11 is a diagrammatic view of reverberation in a pulse inversion multi-pulse ultrasound imaging sequence, according to aspects of the present disclosure.

Some ultrasound imaging modalities that rely on pulse-to-pulse cancellation, such as contrast imaging and tissue harmonics, may be particularly susceptible to reverberation artifacts. FIGS. 9-11 are diagrammatic views of various multi-pulse ultrasound imaging sequences 610, 620, 630, in which reverberation is present. Specifically, FIG. 9 shows an amplitude modulation multi-pulse sequence 610, FIG. 10 shows an amplitude modulation pulse inversion (AMPI) multi-pulse sequence 620, and FIG. 11 shows a pulse inversion sequence 620. In each sequence, multiple transmit pulses are used for a given location (e.g., location −1, location 0, location 1). The transmit pulses may vary in amplitude and/or phase. For example, the amplitude modulation sequence 610 shown in FIG. 9 includes three transmit pulses for each location, wherein the first and third pulses are weighted at 0.5, and the second pulse is weighted at 1.0. When the individual echoes of the pulses are summed in amplitude modulation, the linear frequency portions of the echo signals cancel out while the nonlinear portions remain. However, referring again to FIG. 9, reverberation 612 induced by one pulse in the sequence 610 at a given location may spill over to other receive lines in the same location, or to receive lines at a subsequent location. Thus, standard 3-pulse amplitude modulation implementations may effectively cancel stationary linear signals, but may not cancel signals caused by reverberation. Referring to FIGS. 10 and 11, other multi-pulse sequences such as the AMPI 620 and pulse inversion 630 sequences, may more effectively cancel some, but not all artifacts caused by reverberation 622, 632. For example, in AMPI 620 and pulse inversion 630, reverberation artifacts may be present in the resulting images if (1) the inter- and intra-pulse intervals are different such that the reverb instances are offset relative to each other; (2) a three-pulse inversion scheme is used to handle motion 'flash' artifact; or (3) when differential harmonics are used in pulse inversion to produce two sets of data (e.g., (pulse 1+pulse 2) and (pulse 1−pulse 2)).

Figure 12:
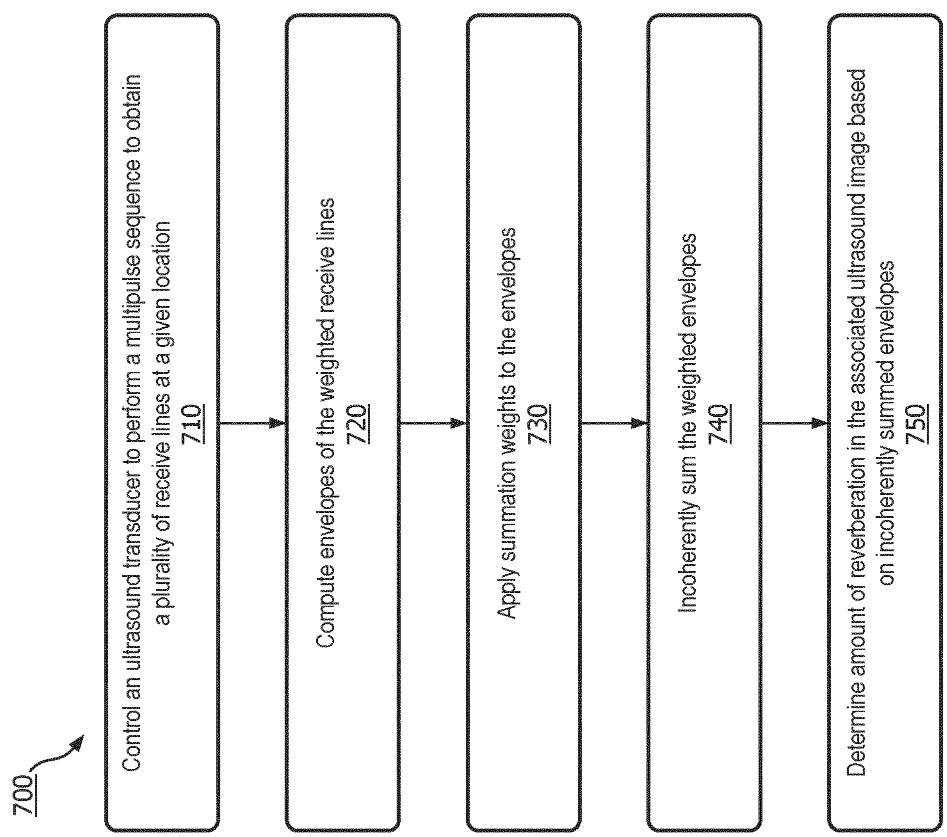
FIG. 12 is a flow diagram illustrating a method for determining an amount of reverberation artifacts in an ultrasound image, according to aspects of the present disclosure.

While multi-pulse sequences may produce reverberation artifacts, reverberation techniques can be used to detect reverberation in the resulting images using weighted sums of the individual pulses in the sequence. In that regard, FIG. 12 is a flow diagram of a method 700 for detecting reverberation in a multi-pulse sequence. It will be understood that one or more steps of the method 700 may be performed by the ultrasound imaging system 100 shown in FIG. 1, and/or the processor circuit 150 shown in FIG. 2, for example. In some aspects, one or more steps of the method 400 may be used in performing the method 300 shown in FIG. 4. For example, the steps of the method 700 may be used in performing steps 310 and/or 320 of the method 300, in some aspects. In step 710, a processor circuit or processing system controls an ultrasound transducer to perform a multi-pulse sequence to obtain a plurality of receive lines at a given location. The receive lines comprise echo signals induced by respective transmit pulses of the sequence. In some embodiments, the transmit pulses of the multi-pulse sequence may be weighted differently, including weights of 0.5, 1.0, −0.5, 1.0, 0.33, or any other suitable weight, both larger and smaller. A pulse with a weight of −1.0, for example, may represent the inverse of the wave form of a pulse with a weight of 1.0.

In step 720, the processor circuit computes envelopes of each of the receive lines. In some aspects, computing the envelopes of the receive lines may include applying an analog and/or digital function or operation to the receive lines. For example, in some embodiments, computing the envelopes may include applying a Hilbert transform to the signal lines. In some aspects, computing the envelopes of the receive lines may include sampling and/or digitizing the receive line signal. In some aspects, the receive line signals may be digitized before the envelope is computed.

In step 730, summation weights are applied to the first and second computed envelopes. In step 740, the weighted envelopes are incoherently summed to produce a summed receive line. It will be understood that incoherent summation refers to summation of envelopes that have lost phase information as opposed to coherent summation of receive lines in which the phase information is present in the summation. In some embodiments, the summation weights are applied to the envelopes in step 730 such that the non-reverberation portions of the envelopes, such as tissue signals, are canceled out while the reverberation portions of the envelopes remain. For example, in some embodiments, a first summation weight of −1.0 is applied to a first envelope and a second summation weight of 1.0 is applied to a second envelope. The opposite signs and equal magnitudes of the summation weights can cause signal portions common to each envelope to cancel out, while signal portions that differ between the first envelope and the second envelope remain.

Figure 13:
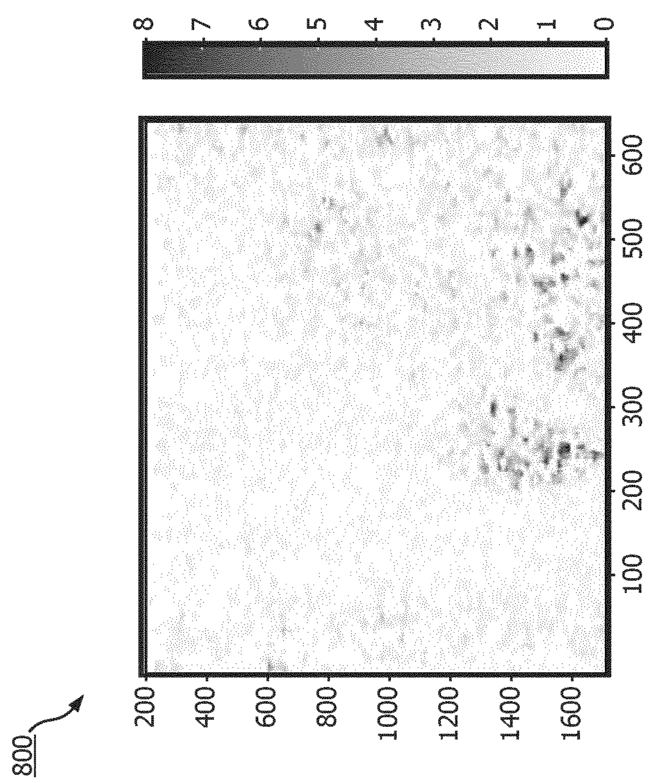
FIG. 13 is an ultrasound image obtained using a multi-pulse sequence and filtered to show quantified reverberation artifacts, according to aspects of the present disclosure.

In some aspects, steps 720-740 may be performed to generate a summed receive line representative of reverberation at a given location in a three-pulse sequence according to the following formula:

$$\text{Reverb} = SumWeight1(\text{envelope}(ReceiveLine1)) + SumWeight2(\text{envelope}(ReceiveLine2)) + SumWeight3(\text{envelope}(ReceiveLine3))$$

where SumWeight1, SumWeight2, and SumWeight3 are the summation weights for the respective first, second, and third envelopes of the corresponding weighted receive lines. The formula above computes the intensity and depth of reverberation at a given location or scan line. By computing the reverberation for each location or scanline (e.g., location −1, 0, 1, FIGS. 9-11) in an ultrasound image, the amount of reverberation in an ultrasound image or field of view is be determined, computed, estimated, and/or mapped in step 750. In that regard, FIG. 13 is a map or image 800 that is filtered to show only the reverberation artifacts in an ultrasound image using the method 700 and formula described above. It can be observed that the reverberation is stronger or more intense in the deeper portions of the image. In some embodiments, the amount of reverberation quantified using the method 700 can be used in a method (e.g., 300, FIG. 4) for automatically controlling the PRI or selecting a pulse sequence or configuration of an ultrasound transducer to reduce the amount of reverberation artifacts in an image. In other embodiments, the method 700 may be used to identify the location and amount of reverberation artifacts in an image so that the reverberation artifacts may be subtracted or removed from an image, with or without adjusting the PRI or changing the pulse sequence.

It will be understood that a similar formula as used above may be used for other multi-pulse sequences that use fewer or more pulses at a given location, such as pulse inversion. For example, the equation above may be modified to include the third receive line and third summation weight to compute the amount of reverberation at a given location. The method 700 and/or formula discussed above may be used with respect to the multi-pulse sequences 610, 620, and 630 illustrated in FIGS. 9-11. For example, for the amplitude modulation multi-pulse sequence 610 illustrated in FIG. 9, which includes first, second and third receive lines corresponding to first, second, and third transmit pulses, the formula above may be applied using summation weights (0, −1, 2) respectively for the first, second, and third envelopes, such that only the second and third envelopes of the weighted receive lines are taken into account. Alternatively, summation weights (1, −1, 1) could also be used to achieve similar results. For the AMPI sequence 620 shown in FIG. 10, the formula above may be applied using summation weights (0, −1, 2), as in the amplitude modulation sequence 610. For the PI sequence 630 shown in FIG. 11, the formula above may be applied using summation weights (1, −1). Accordingly, the summation weights applied to each receive line in a multi-pulse sequence may be selected or configured based on the type of multi-pulse sequence applied, and the transmit weights applied to the corresponding transmit pulses. In some embodiments, the summation weights applied may be based on a ratio of the amplitudes of the different receive lines. For example, in a two-pulse sequence in which the first transmit pulse comprises a first amplitude and the second transmit pulse comprises a second amplitude, the first summation weight is determined or selected based on a ratio of the second amplitude to the first amplitude, and the second summation weight is determined based on a ratio of the first amplitude to the second amplitude. Further, in some embodiments, different weighting sets could be combined to generate a more robust calculation of reverberation, such as an average or geometric mean of different metrics. In some embodiments, different receive weights may be applied to the receive lines before or after the envelope is computed. For example, different combinations of receive weights and/or summation weights may be selected and used to accommodate different types of multi-pulse sequences.

Figure 14:
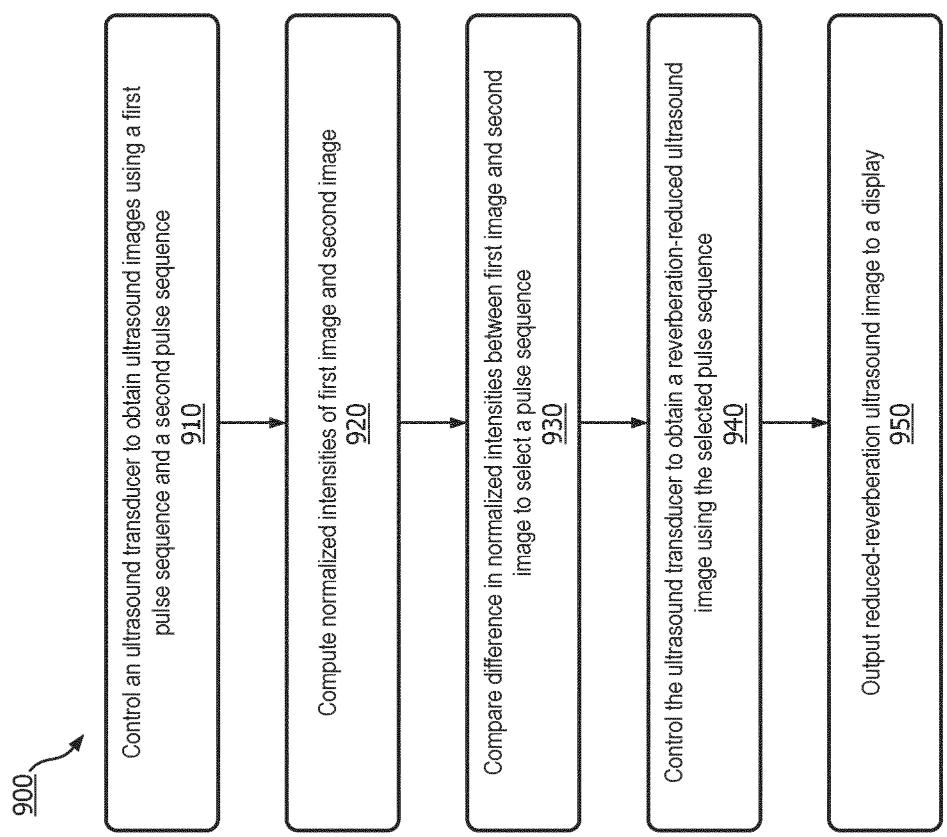
FIG. 14 is a flow diagram illustrating a method for reducing reverberation artifacts in an ultrasound image, according to aspects of the present disclosure.

FIG. 14 is a flow diagram of a method 900 for controlling an ultrasound transducer to reduce reverberation artifacts in ultrasound images by selecting between different ultrasound pulse sequences or configurations. In step 910, a processor circuit controls an ultrasound transducer to obtain ultrasound images using a first pulse sequence, and to obtain ultrasound images using a second pulse sequence. The first and second pulse sequences are different, and may include one or more of a single pulse sequence, amplitude modulation, pulse inversion, AMPI, or any other suitable pulse sequence. In some embodiments, step 910 may include obtaining a first ultrasound image with a single pulse or standard imaging sequence, and obtaining a second ultrasound image using a multi-pulse sequence configured to automatically reduce reverberation artifacts. In step 920, the processor circuit analyzes the obtained ultrasound images using, for example, image processing and analysis techniques, to compute normalized intensity values of the first ultrasound image obtained using the first pulse sequence and the second ultrasound image obtained using the second pulse sequence. In some embodiments, computing the normalized intensity values includes using tissue-suppression techniques as described above with respect to the method 400. In some embodiments, instead of or in addition to computing the normalized intensity values, the steps of the method 700 can be employed to calculate the amount of reverberation artifacts in each ultrasound image.

In step 930, the intensity values of the first and second images are compared to select a pulse sequence or configuration. In some embodiments, the pulse sequence associated with the lowest amount of reverberation artifacts or normalized intensity is selected. In some embodiments, comparing the intensity values includes comparing the intensity or reverberation artifact values to a threshold. For example, in some embodiments, a threshold is selected according to the steps of the method 400, for example, and a pulse sequence or configuration is selected based on the comparison to the threshold. In some aspects, the threshold may represent a degree of change in reverberation artifacts from the current pulse sequence, or first pulse sequence. If the change in reverberation artifacts resulting from the second pulse sequence does not exceed the threshold, the processor circuit may select the current or first pulse sequence, even if some reduction in reverberation artifacts occurs with the second pulse sequence. In other embodiments, the processor circuit may select the second pulse sequence if the second pulse sequence leads to any reduction reverberation artifacts.

In step 940, the processor circuit controls the ultrasound transducer to obtain a reverberation-reduced ultrasound image using the selected pulse sequence or configuration. In step 950, the processor circuit outputs the reverberation-reduced ultrasound image to a display. It will be understood that, in some embodiments, the processor circuit may perform the steps of the method 900 automatically, with little or no input from a user. For example, in some embodiments, a user initiates the method using a user input device (e.g., a keyboard, mouse, trackball, touch screen, etc.), and the processor circuit executes computer program code to carry out the steps of the method 900. In some embodiments, the performance of the individual steps of the method 900 may not be visible to the user (i.e. output to the display) until the reduced-reverberation image is displayed. In other embodiments, the processor circuit may generate one or more graphical representations indicating the individual steps of the method 900. In some embodiments, additional pulse sequences are performed to obtain additional ultrasound images used to select a multi-pulse sequence. For example, two, three, four, five, ten, or more sequences of different types and/or having different configurations and parameters may be used to select a pulse sequence and/or configuration associated with a reduction in reverberation artifacts.

It will be understood that one or more of the steps of the methods 300, 400, 700, 900 described above, such as controlling the array to obtain ultrasound images using a plurality of PRIs, pulse sequences and/or configurations, calculating the amount of reverberation artifacts in each ultrasound image, selecting a PRI, pulse sequence and/or configuration, and any other step may be performed by one or more components of an ultrasound imaging system, such as a processor or processor circuit, a multiplexer, a beamformer, a signal processing unit, an image processing unit, or any other suitable component of the system. For example, one or more steps described above may be carried out by the processor circuit 150 described with respect to FIG. 2. The processing components of the system can be integrated within the ultrasound imaging device, contained within an external console, or may be a separate component.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An apparatus for reducing reverberation artifacts in an ultrasound image, comprising:

a processor circuit in communication with an ultrasound transducer, wherein the processor circuit is configured to:

control the ultrasound transducer to obtain a plurality of ultrasound images using a respective plurality of pulse repetition intervals;

calculate an amount of reverberation artifacts in each of the plurality of ultrasound images;

select a pulse repetition interval based on the amounts of reverberation artifacts in each of the plurality of ultrasound images;

in response to selecting the pulse repetition interval, control the ultrasound transducer to obtain a reduced- reverberation ultrasound image at the selected pulse repetition interval; and output the reduced-reverberation ultrasound image to a display in communication with the processor circuit.

2. The apparatus of claim 1, wherein the processor circuit is configured to:

identify a tissue portion and a non-tissue portion of each of the plurality of ultrasound images;

calculate an intensity value for the non-tissue portion of each of the plurality of ultrasound images; and determine the amount of reverberation artifacts in each of the plurality of ultrasound images based on the calculated intensity values of the non-tissue portions of the plurality of ultrasound images.

3. The apparatus of claim 2, wherein the processor circuit is configured to calculate the intensity value for the non-tissue portion of each of the plurality of ultrasound images using a weighting algorithm, such that a first region of a respective ultrasound image near a focal point of the respective ultrasound image is assigned a greater weight than a second region of the respective ultrasound image away from the focal point of the respective ultrasound image.

4. The apparatus of claim 1, wherein the processor circuit is configured to:

compare the amounts of reverberation artifacts in each of the plurality of ultrasound images to a threshold; and select the pulse repetition interval based on the comparison of the amounts of reverberation artifacts to the threshold.

5. The apparatus of claim 4, wherein the processor circuit is configured to determine the threshold based on the amount of reverberation artifacts in an ultrasound image of the plurality of ultrasound images associated with a maximum pulse repetition interval of the plurality of pulse repetition intervals.

6. The apparatus of claim 4, wherein the processor circuit is configured to select the pulse repetition interval based on:

the comparison of the amounts of reverberations artifacts to the threshold; and a predetermined maximum pulse repetition interval.

7. The apparatus of claim 1, further comprising the ultrasound transducer.

8. The apparatus of claim 1, wherein the processor circuit is configured to:

control the ultrasound transducer to obtain the plurality of images by performing a multi-pulse sequence to obtain a plurality of receive lines at a given location;

sum the plurality of receive lines incoherently; and determine the amount of reverberation artifacts based on the incoherent summation of the plurality of receive lines.

9. The apparatus of claim 8, wherein the plurality of receive lines comprises a first receive line and a second receive line, and wherein the processor circuit is configured to sum the plurality of receive lines incoherently by:

computing:

a first envelope for the first receive line; and a second envelope for the second receive line;

weighting:

the first envelope with a first summation weight; and the second envelope with a second summation weight; and incoherently summing the first weighted envelope and the second weighted envelope.

10. The apparatus of claim 9, wherein:

the first receive line corresponds to a first transmit pulse having a first amplitude, the second receive line corresponds to a second transmit pulse having a second amplitude, and the first and second summation weights are selected based on a ratio of a first amplitude of a first transmit pulse and a second amplitude of a second transmit pulse.

11. A method for reducing reverberation artifacts in an ultrasound image, comprising:

controlling an ultrasound transducer to obtain a plurality of ultrasound images using a respective plurality of pulse repetition intervals;

calculating an amount of reverberation artifacts in each of the plurality of ultrasound images;

selecting a pulse repetition interval based on the calculated amounts of reverberation artifacts in each of the plurality of ultrasound images;

in response to selecting the pulse repetition interval, controlling the ultrasound transducer to obtain a reduced-reverberation ultrasound image at the selected pulse repetition interval; and outputting the reduced-reverberation ultrasound image to a display.

12. The method of claim 11, further comprising:

identifying a tissue portion and a non-tissue portion of each of the plurality of ultrasound images;

calculating an intensity value for the non-tissue portion of each of the plurality of ultrasound images; and calculating the amount of reverberation artifacts in each of the plurality of ultrasound images based on the calculated intensity values of the non-tissue portions of the plurality of ultrasound images.

13. The method of claim 12, wherein calculating the intensity value for the non-tissue portion of each of the plurality of ultrasound images comprises calculating the intensity value for the non-tissue portion of each of the plurality of ultrasound images using a weighting algorithm, such that a first region of a respective ultrasound image near a focal point of the respective ultrasound image is assigned a greater weight than a second region of the respective ultrasound image away from the focal point of the respective ultrasound image.

14. The method of claim 11, further comprising:

comparing the amounts of reverberation artifacts in each of the plurality of ultrasound images to a threshold; and selecting the pulse repetition interval comprises selecting the pulse repetition interval based on the comparison of the amounts of reverberation artifacts to the threshold.

15. The method of claim 14, further comprising determining the threshold based on the amount of reverberation artifacts in an ultrasound image of the plurality of ultrasound images associated with a maximum pulse repetition interval of the plurality of pulse repetition intervals.

16. The method of claim 14, wherein selecting the pulse repetition interval comprises selecting the pulse repetition interval based on:

the comparison of the amounts of reverberations artifacts to the threshold; and a predetermined maximum pulse repetition interval.

17. The method of claim 11, wherein controlling the ultrasound transducer to obtain the plurality of ultrasound images comprises:

performing a multi-pulse sequence to obtain a plurality of receive lines at a given location;

summing the plurality of receive lines incoherently; and determining the amount of reverberation artifacts based on the incoherent summation of the plurality of receive lines.

18. The method of claim 17, wherein the plurality of receive lines comprises a first receive line and a second receive line, and wherein summing the plurality of receive lines incoherently comprises:

computing:

a first envelope for the first receive line; and a second envelope for the second receive line;

weighting:

the first envelope with a first summation weight; and the second envelope with a second summation weight; and incoherently summing the first weighted envelope and the second weighted envelope.

19. The method of claim 18, wherein:

the first receive line corresponds to a first transmit pulse having a first amplitude, the second receive line corresponds to a second transmit pulse having a second amplitude, and the first and second summation weights are selected based on a ratio of a first amplitude of a first transmit pulse and a second amplitude of a second transmit pulse.

20. An apparatus for selecting a pulse sequence associated with reduced reverberation artifacts, comprising:

a processor circuit in communication with an ultrasound transducer, wherein the processor circuit is configured to:

control the ultrasound transducer to obtain a first ultrasound image using a first pulse sequence;

control the ultrasound transducer to obtain a second ultrasound image using a second pulse sequence;

calculate an amount of reverberation artifacts in each of the first ultrasound image and the second ultrasound image;

compare the amounts of reverberation artifacts of the first ultrasound image and the second ultrasound image;

select a pulse sequence based on the comparison of the amounts of reverberation artifacts;

control the ultrasound transducer to obtain a reduced-reverberation ultrasound image using the selected pulse sequence; and output the reduced-reverberation ultrasound image to a display in communication with the processor circuit.

* * * * *